United States Patent [19]

Mann et al.

[11] Patent Number: 4,626,212
[45] Date of Patent: Dec. 2, 1986

[54] DENTAL INSTRUMENT

[76] Inventors: Harris Mann, 3518 Dows Rd., Philadelphia, Pa. 19154; Jeffrey M. Cohen, 1311 Huntingdon Pike, Huntingdon Valley, Pa. 19006

[21] Appl. No.: 696,765

[22] Filed: Jan. 31, 1985

[51] Int. Cl.⁴ ............................................. A61C 3/02
[52] U.S. Cl. .................................................. 433/144
[58] Field of Search ................. 433/143, 144, 141; 30/339, 338, 336; 128/305

[56] References Cited

U.S. PATENT DOCUMENTS

| 208,582 | 10/1878 | Fenton | 30/346 |
|---|---|---|---|
| 756,138 | 3/1904 | Petersen . | |
| 840,748 | 1/1907 | Cafferty | 30/338 |
| 990,882 | 5/1911 | Kratz | 30/338 |
| 1,913,598 | 6/1933 | Keefe . | |
| 3,683,498 | 8/1972 | Riley | 30/339 |
| 3,771,537 | 11/1973 | Schole . | |
| 4,259,069 | 3/1981 | Lustig | 433/144 |
| 4,377,381 | 3/1983 | Westman . | |

FOREIGN PATENT DOCUMENTS 37262  6/1906  Switzerland ................. 30/346

Primary Examiner—Robert Peshock
Attorney, Agent, or Firm—Z. T. Wobensmith, III

[57] ABSTRACT

A dental instrument is provided for the mechanical removal of plaque and/or other material from or adjacent to a patient's teeth, both above and below the gum line, which instrument includes a hollow plastic handle with an angularly related shank extending therefrom, which carried an integral single or double sided blade for removal of material, and which instrument is intended for single patient use and to be discarded thereafter.

2 Claims, 12 Drawing Figures

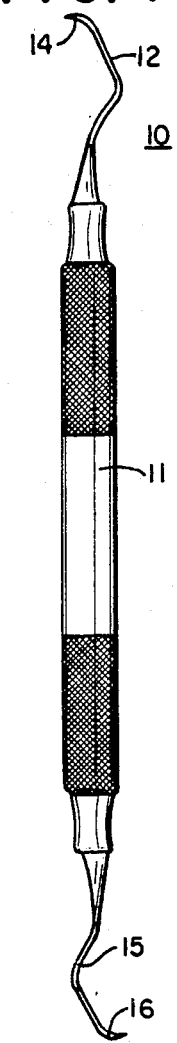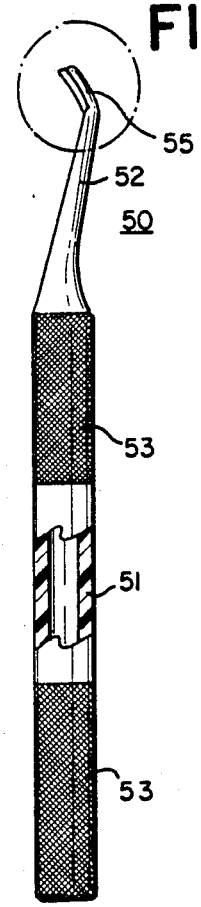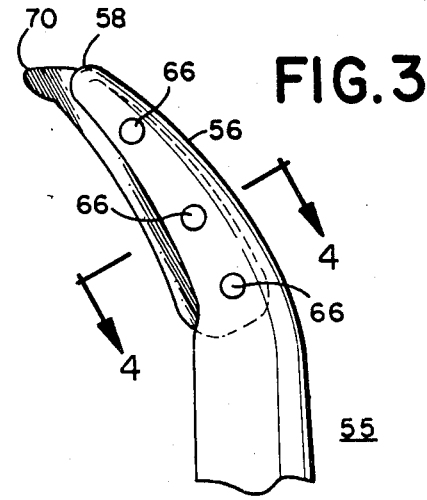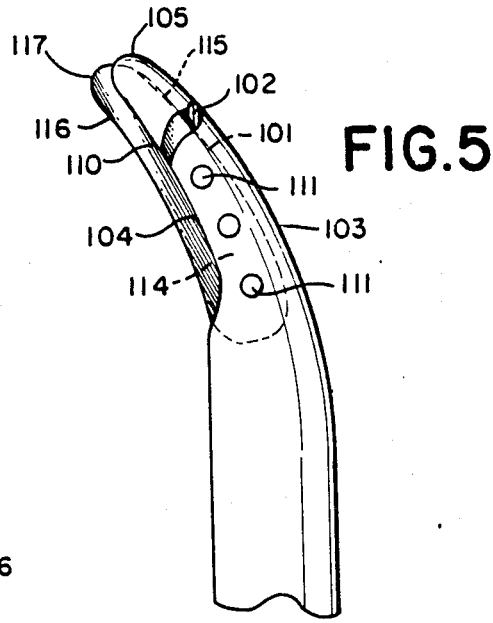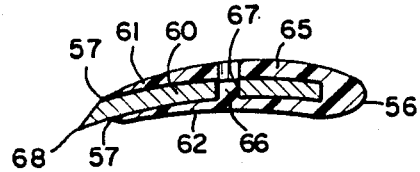

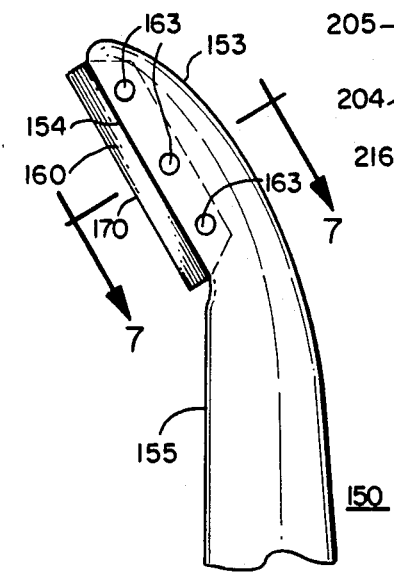
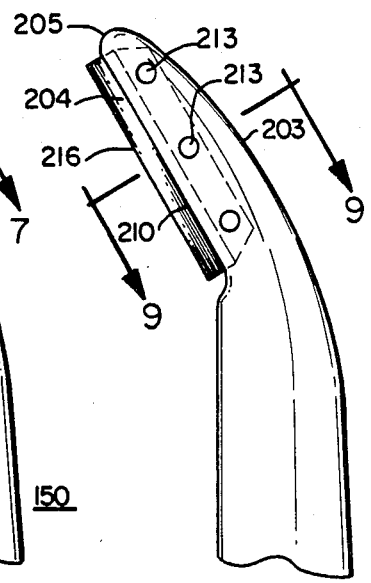
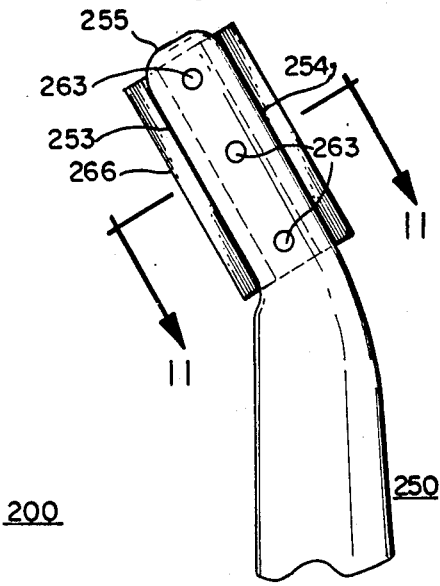
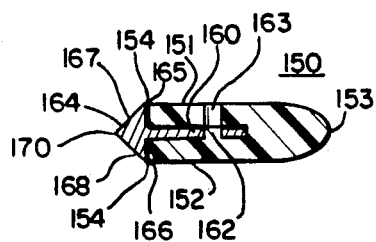
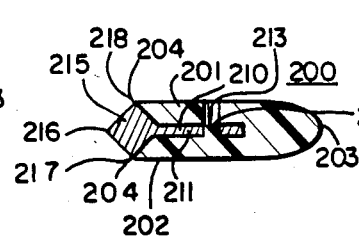
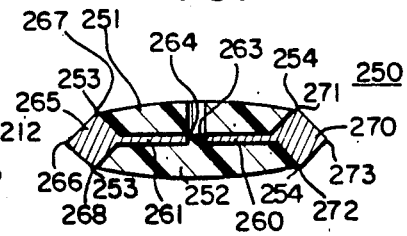
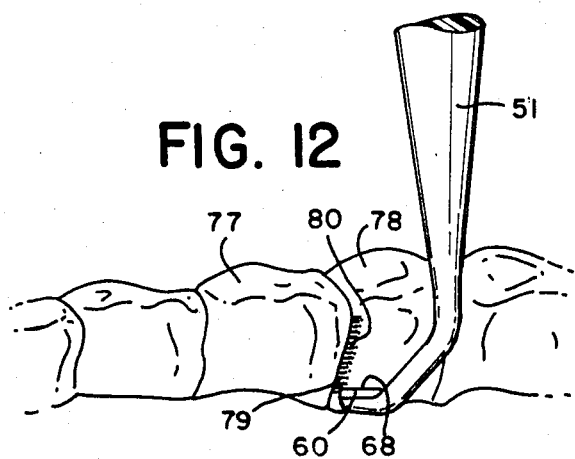

4,626,212

DENTAL INSTRUMENT

BACKGROUND OF THE INVENTION

1. Field of the Invention

This invention relates to a hand held mechanical dental instrument for removal of material from or about the teeth of a patient, which is of the type which includes a shaft with an angularly related shank extending therefrom carrying a single or double edged blade.

2. Description of the Prior Art

The removal of plaque and/or other material from or about the teeth of patients is routinely performed by dentists, and considered essential to good dental care and the proper maintenance of teeth.

Some of the procedures that the dentist performs by using hand held instruments involves scaling and root planning for the purpose of removing plaque, calculus, granulation tissue and necrotic cementum. The dental procedures commonly involve instruments that are highly specific for both supra and sub-gingival areas, in that they are geometrically oriented to these areas, and must maintain a minimal rate of abrasion and possess high shear stress.

The instruments available to the dentist for material removal prior to those to be described below, are mostly constructed of stainless steel, are heavy, are designed to be sharpened and must be autoclaved or sterilized between uses. A dentist who is engaged in a clinic type practice, where a high volume of patients are treated, must maintain a large quantity of clean sharp instruments at all times.

Due to the prevalence of highly transmissable diseases, such as Hepatitis B, there is a greater possibility of contaminating non-disposable instruments and therefore creating an inadequate aseptic environment. The expense of instrument replacement is high due to manufacturing costs. Sharpening of the instruments is frequent, takes considerable time, and must be done very precisely due to angulation of blade, therefore increases costs.

Various devices have been proposed for cleaning both natural and artificial teeth.

The U.S. Pat. No. to Petersen 756,138 discloses a tooth brush having a thin metal plate in the handle, which is designed to go between the teeth and remove material therebetween, but is not suitable for other periodontal procedures.

The U.S. Pat. No. to Keefe 1,913,598 discloses a dental instrument which includes a thin pliant sheet of metal, which may have a serrated edge, and a backing of less pliant material. The thin sheet is intended to be inserted between teeth at the contact points to remove decay or other material, but is not suitable for other periodontal procedures.

The U.S. Pat. No. to Schole 3,771,537 discloses a method and device for mechanical cleaning of teeth which involves the use of a round-edged, non-cutting flexible blade which has a thickness which approximates that of the inter-proximal spacing of adjoining, contacting teeth. The blade is inserted between the teeth and slid back and forth between contacting teeth. While this device may be useful for removing plaque between teeth, it is not suitable for other periodontal procedures.

The U.S. Pat. No. to Westman 4,377,381 discloses a tool for use by a denture wearer to remove unwanted material from dentures. The tool includes a square handle with a spear shaped blade extending from one end and a convex-concave rounded tip blade extending from the other end. While this tool may be useful for removing plaque or other material from dentures, it is not suitable for periodontal procedures in the mouth of the patient.

The dental instrument of the invention is suitable for periodontal and other procedures, and possesses many advantages not found in prior available instruments.

SUMMARY OF THE INVENTION

This invention relates to a hand held dental instrument for the mechanical removal of plaque and other material from teeth or about teeth, above and below the gum line, and includes a hollow handle with an angularly related shank extending therefrom which carries a single or double edged blade.

The principal object of the invention is to provide a dental instrument that can be used for a variety of surgical and non-surgical procedures.

A further object of the invention is to provide a dental instrument which is of light weight and provides improved tactile sense.

A further object of the invention is to provide a dental instrument that is economical to manufacture, and which provides an improved character of operation.

A further object of the invention is to provide a dental instrument that can be pre-sterilized and packaged for use.

A further object of the invention is to provide a dental instrument which is intended for a single use and then may be discarded.

Other objects and advantageous features of the invention will be apparent from the description and claims.

DESCRIPTION OF THE DRAWINGS

The nature and characteristic features of the invention will be more readily understood from the following description taken in connection with the accompanying drawings forming part hereof in which:

FIG. 1 is a side elevational view of a prior art dental instrument;

FIG. 2 is a side elevational view of the dental instrument of the invention;

FIG. 3 is a fragmentary view, enlarged, of a portion of the dental instrument of FIG. 2;

FIG. 4 is a horizontal sectional view, still further enlarged, taken approximately on the line 4—4 of FIG. 3;

FIG. 5 is a view similar to FIG. 3 showing another embodiment of the invention;

FIG. 6 is a view similar to FIG. 3 showing another embodiment of the invention;

FIG. 7 is a horizontal sectional view, enlarged, taken approximately on the line 7—7 of FIG. 6;

FIG. 8 is a view similar to FIG. 3 showing another embodiment of the invention;

FIG. 9 is a horizontal sectional view, enlarged, taken approximately on the line 9—9 of FIG. 8;

FIG. 10 is a view similar to FIG. 3 showing still another embodiment of the dental instrument of the invention;

FIG. 11 is a horizontal sectional view, enlarged, taken approximately on the line 11—11 of FIG. 10; and FIG. 12 is a side view of the dental instrument of FIG. 2 illustrating its use in removing material from teeth.

It should, of course, be understood that the description and drawings herein are illustrative merely and that various modifications and changes can be made in the structure disclosed without departing from the spirit of the invention.

DESCRIPTION OF THE PREFERRED EMBODIMENTS

Referring now more particularly to the drawings and FIG. 1 thereof, a prior art dental instrument 10 is illustrated, which includes a shaft 11 of cylindrical shape with a hook shaped shank 12 extending upwardly, and which has a sharpened cutting edge 14 for scraping of plaque or other material from one side of a tooth (not shown). The dental instrument 10 also has another hook shaped shank 15 extending downwardly therefrom, with a sharpened cutting edge 16 for scraping of plaque or other material from the opposite side of a tooth (not shown) from that of edge 14. The dental instrument 10 is well known in the art, is usually constructed of stainless steel, has been in use for many years, and forms no part of the invention. The instrument 10 is typical of available prior art reusable instruments, with the stated disadvantages of heavy weight, necessity of frequent sharpening, and which must be sterilized between patients to prevent the transmission of disease.

Referring now more particularly to FIGS. 2–4 and 12 inclusive, one embodiment of the dental instrument 50 of the invention is therein illustrated, which includes a shaft 51 of hollow molded construction, and which is preferably of molded synthetic plastic, such as a high-molecular weight polymer of formaldehyde, one suitable synthetic plastic being delrin available from E. I. du Pont de Nemours & Co., Wilmington, Del., or other suitable inert, non-toxic materials can be used as desired. The shaft 51, which is of cylindrical shape, can be provided with knurling 53 to assist the user (not shown) in gripping the instrument for use. The shaft 51 has a shank 52 extending axially therefrom which is angularly offset from the central axis of the shaft 51, and is provided with a tip 55, which is angled back towards the central axis of the shaft 51. The shank 52 is also of molded synthetic plastic and preferably integral with shaft 51.

The tip 55 which is more clearly illustrated in FIGS. 3 and 4, has a curved rear edge 56 and a curved front edge 57, which is set back from the continuation of the normal curvature of shank 52, and which edges 56 and 57 converge to a point 58.

The tip 55 is provided with a blade 60 carried therein between walls 61 and 62 of the tip, the blade 60 being of elongated knife-like configuration, with a central portion 65 carried in and retained between outer walls 61 and 62, by molded studs 66, which extend through holes 67 in blade 60. The blade 60, which is preferably of surgical steel, has a sharpened edge 68 which extends along and is spaced from front edge 57 and which then tapers forward to a finger-like tip extension 70.

Referring now more specifically to FIG. 12, the instrument 50 is shown with shaft 51 grasped between the fingers (not shown) of a user. The tip 55 is inserted between two adjacent teeth 77 and 78 of a patient (not shown) and the edge 68 of blade 60 is thereby in contact with the surface 79 of a tooth 78 for removal of plaque 80, which is on the surface 79. The instrument 50, in use, is moved upwardly with blade edge 68 scraping the plaque 80 off the tooth surface 79. It should be noted that the walls 61 and 62 are tapered towards blade 60 as seen in FIG. 4 so that a smooth fit is made with the blade 60.

Referring now more particularly to FIG. 5, another embodiment of tip 100 is illustrated which is preferably of molded plastic, with outer walls 101 and 102. The tip 100 has a curved rear edge 103 and a front edge 104 which extend forwardly, converging to a point 105. A blade 110 is provided between walls 101 and 102, with molded studs 111 extending through holes (not shown) in the central portion 114 of blade 110, to retain it in the same manner as blade 60 is retained in tip 55.

The blade 110, preferably also of surgical steel like blade 60, has a rear edge 115 and a front edge 116 which front edge 116 is sharpened, the edges 115 and 116 converging at a rounded tip 117. The outer walls 101 and 102 are tapered on their front edges 104 where they meet the blade 110, to provide a smooth meeting surface with blade 110.

Referring now more particularly to FIGS. 6 and 7, another embodiment of tip 150 is illustrated which includes outer walls 151 and 152 of molded synthetic plastic, like that used for tip 55, which walls meet at a curved rear edge 153, and extend forward to front edges 154 which are straight edges, and set back from a normal continuation of edge 155 of tip 150. A blade 160, preferably of surgical steel, is provided which includes a central portion 161, and is retained between walls 151 and 152 by molded studs 162 which extend through holes 163 in blade 160. The blade 160 has a front triangularly shaped portion 164 which is integral with and extends from central portion 161, with walls 165 and 166 which meet front edges 154 and with walls 167 and 168 extending therefrom and forwardly to a sharpened edge 170.

Referring now more particularly to FIGS. 8 and 9, another embodiment of tip 200 is illustrated which includes outer walls 201 and 202 of molded synthetic plastic like that for tip 55. The walls 201 and 202 meet at a curved rear edge 203 and terminate at front edges 204 and taper forwardly to a rounded tip 205.

A blade 210, preferably of surgical steel, is provided which has a central portion 211, which is retained between walls 201 and 202 by molded studs 212, which are engaged in holes 213 in central portion 211 of blade 210. The blade 210 has a square shaped front portion 215, integral with and extending from the central portion 211, with three exposed corner edges 216, 217, and 218. The corner edges 217 and 218 meet the front edges 204 of walls 201 and 202, and the edge 216 is a sharpened edge.

Referring now more particularly to FIGS. 10 and 11, still another embodiment of tip 250 is illustrated which includes outer walls 251 and 252 of molded synthetic plastic like that for tip 55. The walls 251 and 252 are symetrical, with front edges 253 and rear edges 254. The walls 251 and 252 meet at a rounded front tip 255.

A blade 260, preferably of surgical steel, is provided with a central portion 261 which extends across tip 250 between the walls 251 and 252. The blade 260 is retained therein by molded studs 263 which are engaged in holes 264 in central portion 261 of blade 260.

The blade 260 has a square shaped front portion 265 similar to front portion 215 of blade 210, with three exposed corner edges 266, 267, and 268. The edges 267 and 268 meet the front edges 253 of walls 251 and 252 and the edge 266 is a sharpened edge. The blade 260 includes a square shaped rear portion 270 with edges 271, 272 and 273, which is similar to front portion 265, but which is of the opposite hand from that of portion 265 permitting the sharpened edge 273 to perform scraping and curettage operations.

It should be noted that the sharpened edges 68, 116, 170 and 216 of blades 60, 110, 160, and 210 are used in the normal manner for scraping sides of teeth from outside the mouth by the dentist or other user to remove plaque, calculus, granulation tissue and necrotic cementum. The same operation is available for blade 260 but can also be used for curettage. The small size of the tips permits them to be inserted between teeth, and as shown in FIG. 12, to remove material both above and below the gum line.

It should be noted that in each of the embodiments described above the tip has spaced parallel walls with inwardly directed surfaces which bear flush against the side surface of the blade inserted therebetween, thereby providing a firm seat for the blade during its use upon the teeth. Since the free edges of the walls on opposite sides of the blade extend closely parallel along the sharpened edge of the blade, they provide the desired support for the cutting edge. Abutment means is provided to cooperate with the walls to provide support against parallel movement between the walls. In the embodiments of FIGS. 3 and 5, the rear edge of the tip provides a bridge between the walls, providing an elongated abutment surface against which the remote edge of the blade may bear during use. In the embodiments of FIGS. 6, 8, and 10 the free edges of the tip adjacent the blade edge provide elongated abutment surfaces which bear against the rear surface of the enlarged angularly cross-sectioned portions which form the sharpened edges of the blades. Those abutment surfaces are generally parallel to the sharpened edge of the blade and are approximately coextensive with the sharpened edge to provide extended support against any movement of the blade perpendicular to its edge during use. The posts or studs engaging in the holes in the blades prevent inadvertent dislodgement of the blades from between the walls and also prevent movement parallel to the abutment surfaces.

Preferably the walls are open at the free end of the tip to permit the insertion of a blade having a forward extension as shown in FIGS. 3 and 5. By housing the blade most completely within the tip, it is firmly held and may be used for root planning and to remove calculus and like material from the teeth as effectively as the solid steel instrument of the prior art. Yet the device of our invention may be manufactured and assembled at a cost which enables the device to be disposed of after a single use. The configuration of the tip relative to the shank ensures that the elongated edges of the tip, which are parallel to the blade edge, face rearwardly at an angle to the longitudinal axis of the handle as shown in FIG. 2 with the free end of the blade being positioned substantially along the extended center line of the tool, thereby facilitating manipulation of the tool in the mouth.

The instrument, which can be inexpensively constructed, is intended for a single use and the blade angle can be fixed for either front or rear surfaces of the teeth, as desired by the dentist or other user.

It will thus be seen that dental instruments have been provided in accordance with the objects of the invention.

We claim:

1. A hand held dental instrument of molded synthetic plastic for the removal of material from or about the teeth of a person which comprises
    a shaft,
    at least one angularly related shank extending from said shaft,
    said shank including a tip having spaced parallel walls,
    blade means having a central portion carried in said tip,
    said central portion having at least two openings,
    studs from said tip extending through said openings for blade retention in said tip,
    said central portion having a front portion of square cross section extending along its length, and
    said square front portion providing one exposed sharpened cutting edge, and providing two abutment surfaces opposite said edge.

2. A dental instrument as defined in claim 1 in which
    said central portion also has a rear portion of square cross section extending along its length, and
    said square shaped rear portion providing an additional exposed sharpened cutting edge, and providing two additonal abutment surfaces opposite said additional edge.

* * * * *